United States Patent [19]

Chou

[11]  4,159,272
[45]  Jun. 26, 1979

[54] PROCESS FOR 2-CHLOROSULFINYLAZETIDIN-4-ONES

[75] Inventor: Ta-Sen Chou, Indianapolis, Ind.

[73] Assignee: Eli Lilly and Company, Indianapolis, Ind.

[21] Appl. No.: 829,689

[22] Filed: Sep. 1, 1977

[51] Int. Cl.$^2$ .................. C07D 333/24; C07D 333/38
[52] U.S. Cl. ........................ 260/332.2 A; 260/239 A; 260/332.2 H; 260/347.2
[58] Field of Search ................ 260/332.2 H, 332.2 A, 260/347.2, 239 A, 239.1

[56] References Cited

U.S. PATENT DOCUMENTS

| | | | |
|---|---|---|---|
| 3,843,682 | 10/1974 | Kukolja et al. | 260/243 C |
| 4,075,203 | 2/1978 | Chou | 544/18 |
| 4,081,440 | 3/1978 | Kukolja | 544/18 |

Primary Examiner—Gerald A. Schwartz
Attorney, Agent, or Firm—William B. Scanlon; Arthur R. Whale

[57] ABSTRACT

Penicillin sulfoxide esters having the sulfoxide group in the α-configuration are reacted with an N-chloro halogenating agent at a temperature between about 70° C. and about 120° C. in the presence of an alkylene oxide and preferably also calcium oxide to produce 2-chlorosulfinyl-azetidin-4-one intermediates. The chlorosulfinyl intermediates are then treated with a Friedel-Crafts catalyst, for example, stannic chloride to provide a 3-exomethylenecepham β-sulfoxide. The latter compounds are useful in the preparation of 3-alkoxy and 3-halo substituted cephalosporin antibiotic compounds.

11 Claims, No Drawings

PROCESS FOR 2-CHLOROSULFINYLAZETIDIN-4-ONES

BACKGROUND OF THE INVENTION

This invention relates to an improved process for the preparation of 3-methyl-2-[2-chlorosulfinyl-4-oxo-3-acylamido-1-azetidinyl]-3-butenoic acid esters represented by the following structural formula.

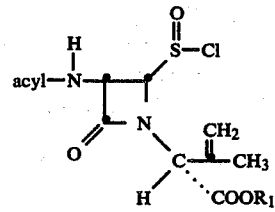

wherein acyl represents the acyl residue of a carboxylic acid and $R_1$ is a carboxy protecting group.

The above esters are referred to herein for convenience as 2-chlorosulfinyl azetidin-4-ones. These azetidinones are useful intermediates in the process for preparing 7-acylamido-3-exomethylenecepham-4-carboxylic acid ester sulfoxides.

Kukolja et al. described, in U.S. Pat. No. 3,843,682 issued Oct. 22, 1974, the preparation of diacylamido chlorosulfinylazetidinones by reacting a 6-diacylamido penicillin sulfoxide ester, for example, p-nitrobenzyl 6-phthalimido-2,2-dimethylpenam-3-carboxylate sulfoxide, with sulfuryl chloride in an inert hydrocarbon solvent such as benzene.

Kukolja, in co-pending application Ser. No. 673,017 filed Apr. 2, 1976 now U.S. Pat. No. 4,081,440, describes the conversion of 6-acylamido penicillin sulfoxide esters to the acylamido 2-chlorosulfinyl azetidin-4-one compounds represented by the above formula by reacting the penicillin sulfoxide with a N-chloro halogenating agent, such as N-chlorosuccinimide, in the presence of an alkylene oxide, such as propylene or butylene oxide. The latter Kukolja process is distinguished from that described in the above-cited U.S. Pat. No. 3,843,682 wherein only 6-diacylamido penicillin ester sulfoxides were converted to the 2-chlorosulfinylazetidinones. In contrast, the latter Kukolja process employs a 6-monoacylamido penicillin sulfoxide ester which previously had not been converted to an azetidinone-type compound.

Later, Ta-Sen Chou in co-pending application Ser. No. 696,674 filed June 16, 1976 now U.S. Pat. No. 4,075,203 described an improved process, over that described by Kukolja, for preparing the acylamido-2-chlorosulfinylazetidin-4-ones on a large scale. The process improvement comprises using calcium oxide in conjunction with one of the alkylene oxides described by Kukolja to obtain enhanced yields particularly in large scale preparations of the 2-chlorosulfinyl compounds.

In co-pending application Ser. No. 673,036 filed Apr. 2, 1976, Kukolja describes the process for converting acylamido 2-chlorosulfinylazetidin-4-ones by a Lewis acid-Friedel-Crafts catalyzed intramolecular cyclization to the 7-acylamido-3-exomethylenecepham-4-carboxylic acid ester sulfoxides represented by the following formula.

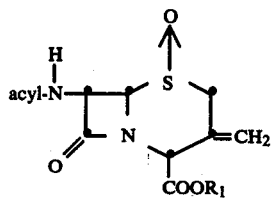

This invention comprises an improvement in the conversion of a 6-acylamido penicillin sulfoxide ester to the corresponding 3-acylamido 2-chlorosulfinylazetidin-4-one intermediate. Previously, the 6-monoacylamido penicillin sulfoxide employed in the above-described processes had the β-configuration represented by the following partial structural formula.

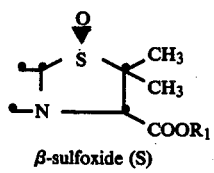

β-sulfoxide (S)

In the above formula of the β-configuration, the sulfoxide oxygen is forward or above the plane.

According to the improved process of this invention, a 6-acylamido-2,2-dimethylpenam-3-carboxylic acid ester sulfoxide wherein the sulfoxide group has the α-configuration as represented by the following structural formula

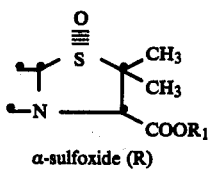

α-sulfoxide (R)

is employed in the above-described process to provide the 2-chlorosulfinylazetidin-4-one intermediate in enhanced yields. The 2-chlorosulfinylazetidin-4-one is converted to a 3-exomethylenecepham sulfoxide ester in improved yields of higher purity material than is obtained in the prior process employing the penicillin sulfoxide ester having the β-configuration.

The proposed course of the above-described process involves initially the thermolysis of the penicillin thiazolidine ring to form the ring-opened sulfenic acid according to the following reaction scheme.

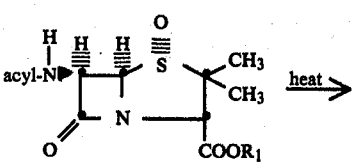

-continued

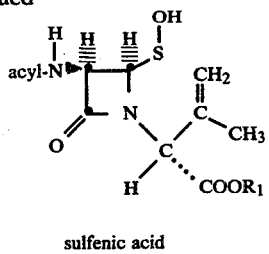

sulfenic acid

The sulfenic acid intermediate then reacts with an N-chloro halogenating agent, for example, N-chlorosuccinimide to provide the 2-chlorosulfinylazetidin-4-one according to the following reaction scheme.

sulfenic acid
+
N-chloro halogenating agent ⟶

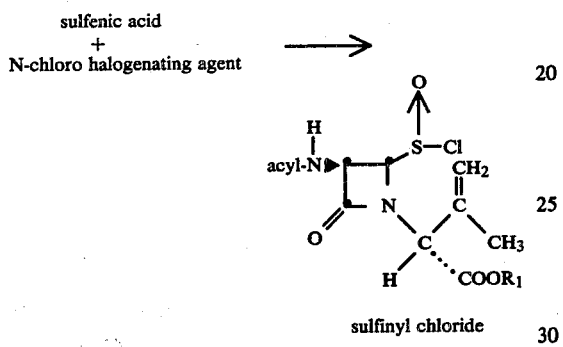

sulfinyl chloride

The sulfinyl chloride is then reacted with a Lewis acid-Friedel-Crafts type catalyst, such as stannic chloride, to effect the intramolecular cyclization with formation of the 7-acylamido-3-exomethylenecepham-4-carboxylic acid ester sulfoxide having the β-configuration as shown in the following reaction scheme.

sulfinyl chloride + SnCl$_4$ ⟶

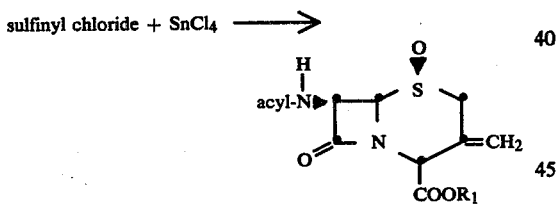

It has been discovered that the penicillin α-sulfoxide undergoes facile cleavage to the sulfenic acid at a lower temperature than does the β-sulfoxide. Further, it has been discovered that the N-chloro halogenating agent reacts instantaneously with the sulfenic acid to provide the sulfinyl chloride. The use of the α-sulfoxide allows the process to be carried out at lower temperatures and over a shorter period of time than does the use of the corresponding penicillin β-sulfoxide. For example, penicillin V α-sulfoxide ester undergoes conversion in 2 hours to the sulfinyl chloride when the process is carried out at a temperature of about 78° C. In contrast penicillin V β-sulfoxide ester requires a temperature of about 110° C. for conversion to the sulfinyl chloride in about 2 hours. Since the process can be carried out faster decomposition products occurring over the longer reaction times with the sulfinyl chloride are diminished. For example, the sulfinyl chloride can react with the starting sulfoxide to form several β-lactam ring opened side products. Or it will disproportionate to give sulfonyl chloride and the unstable sulfenyl chloride which will further decompose. The avoidance of the longer reaction times required with the penicillin β-sulfoxide greatly reduces these side reactions and thus provides higher yields of the intermediate sulfinyl chlorides which are reflected in higher yields of the cyclized 7-acylamido-3-exomethylenecepham-4-carboxylic acid ester β-sulfoxide in a high state of purity.

DETAILED DESCRIPTION

According to the process of this invention, a 6-acylamido-2,2-dimethylpenam-3-carboxylic acid ester α-sulfoxide is heated at a temperature between about 70° C. and about 120° C. and preferably at a temperature between about 75° C. and about 115° C. in an inert organic solvent under anhydrous conditions with an N-chloro halogenating agent to produce an ester of a 3-methyl-2-(2-chlorosulfinyl-4-oxo-3-acylamido-1-azetidinyl)-3-butenoic acid represented by the following structural formula.

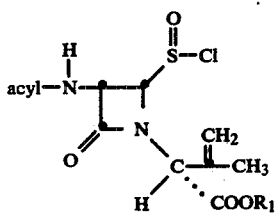

In the above formula the term "acyl" refers to the acyl derivative derived from a carboxylic acid and the term "R$_1$" refers to a carboxylic acid protecting group.

As in the prior process employing the penicillin β-sulfoxide described by Kukolja in co-pending application Ser. No. 673,017, in the process of this invention, a non-alkaline acid scavenger is employed. Non-alkaline acid scavengers are preferably the alkylene oxides such as ethylene oxide, propylene oxide, 1,2-epoxybutane, 1,2-epoxy-3-phenoxypropane, and the like.

The N-chloro halogenating agent employed in the process is represented by the following structural formula.

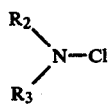

wherein R$_2$ is hydrogen, chloro, C$_1$–C$_3$ alkyl, cyclohexyl, phenyl, or phenyl substituted with chloro, bromo, methyl, or nitro, and R$_3$ is R$_4$—M— wherein R$_4$ is C$_1$–C$_3$ alkyl, cyclohexyl, phenyl, or phenyl substituted with chloro, bromo, methyl, or nitro, and X is

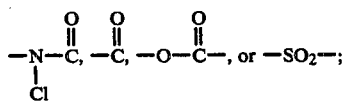

or R$_2$ and R$_3$ taken together with the nitrogen to which they are bonded define a heterocyclic structure of the formula

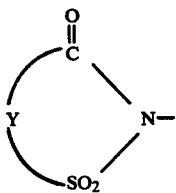

in which Y is o-phenylene or —(CH$_2$)$_n$— in which n is 2 or 3; or a structure of the formula

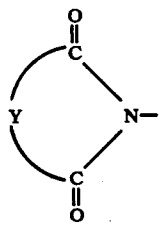

in which Y is as hereinbefore defined.

Several types of preferred N-chloro compounds which can be employed in producing the sulfinyl chlorides are described by the above definition. These N-chloro compounds include (a) ureas, (b) amides, (c) urethans, (d) sulfonamides, (e) sulfimides, and (f) imides.

The preferred N-chloro ureas which can be employed in this invention generally have the formula

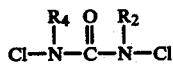

in which R$_2$ is hydrogen, chloro, C$_1$–C$_3$ alkyl, cyclohexyl, phenyl, or phenyl substituted with chloro, bromo, methyl, or nitro, and R$_4$ is C$_1$–C$_3$ alkyl, cyclohexyl, phenyl, or phenyl substituted with chloro, bromo, methyl, or nitro.

Illustrative of these ureas are
N,N'-dichloro-N-methylurea;
N,N'-dichloro-N-ethyl-N'-cyclohexylurea;
N,N'-dichloro-N-phenylurea;
N,N'-dichloro-N,N'-diphenylurea;
N,N'-dichloro-N-(p-tolyl)urea;
N,N'-dichloro-N-(m-chlorophenyl)-N'-methylurea;
N,N'-dichloro-N,N'-dicyclohexylurea;
N,N'-dichloro-N-isopropyl-N'-(p-tolyl)urea;
N,N'-dichloro-N-phenyl-N'-propylurea;
N,N'-dichloro-N-cyclohexyl-N'-(p-nitrophenyl)urea;
N,N,N'-trichloro-N-methylurea;
N,N,N'-trichloro-N-phenylurea; and the like.

The preferred N-chloro amides which can be employed in this invention generally have the formula

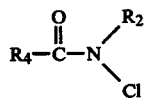

in which R$_2$ and R$_4$ are as hereinbefore defined.

Illustrative of these amides are N-chloroacetamide, N-chloropropionamide, N-chloro-N-methylacetamide, N,N-dichloroacetamide, N-chloro-N-cyclohexylacetamide, N-chloro-N-ethylbenzamide, N-chloro-p-chlorobenzamide, N-chloro-p-toluamide, N-chloro-N-phenylpropionamide, N-chloro-N-(m-bromophenyl)butyramide, N-chlorohexahydrobenzamide, N,2,4-trichloroacetanilide, and the like.

The preferred N-chloro urethans which can be used in preparation of the sulfinyl chlorides in accordance with this invention generally have the formula

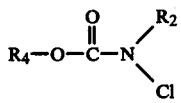

in which R$_2$ and R$_4$ are as hereinbefore defined.

Illustrative of these urethans are methyl N,N-dichlorocarbamate, ethyl N,N-dichlorocarbamate, phenyl N,N-dichlorocarbamate, cyclohexyl N,N-dichlorocarbamate, methyl N-chlorocarbamate, ethyl N-chlorocarbamate, ethyl N-cyclohexyl-N-chlorocarbamate, phenyl N-chlorocarbamate, phenyl N-phenyl-N-chlorocarbamate, p-tolyl N-chlorocarbamate, m-chlorophenyl N-methyl-N-chlorocarbamate, cyclohexyl N-cyclohexyl-N-chlorocarbamate, isopropyl N-p-tolyl-N-chlorocarbamate, phenyl N-propyl-N-chlorocarbamate, cyclohexyl N-p-nitrophenyl-N-chlorocarbamate, and the like.

The preferred N-chloro sulfonamides which can be used to prepare the sulfinyl chlorides in accordance with this invention have the formula

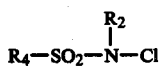

in which R$_2$ and R$_4$ are as hereinbefore defined.

Illustrative of the sulfonamides which can be employed as halogenating agents are N,N-dichlorobenzenesulfonamide, N,N-dichloromethanesulfonamide, N,N-dichlorocyclohexanesulfonamide, N,N-dichloro-p-toluenesulfonamide, N-chloromethanesulfonamide, N-cyclohexyl-N-chlorobenzenesulfonamide, N-cyclohexyl-N-chloroethanesulfonamide, N-chlorobenzenesulfonamide, N-phenyl-N-chlorobenzenesulfonamide, N-chloro-p-toluenesulfonamide, N-ethyl-N-chloro-m-nitrobenzenesulfonamide, N-methyl-N-chloro-m-chlorobenzenesulfonamide, N-methyl-N-chloro-p-toluenesulfonamide, N-cyclohexyl-N-chlorocyclohexanesulfonamide, N-p-tolyl-N-chloroisopropanesulfonamide, N-propyl-N-chlorobenzenesulfonamide, N-p-nitrophenyl-N-chlorocyclohexanesulfonamide, and the like.

A further preferred type of N-chloro halogenating agent which can be employed in preparation of the sulfinyl chlorides is a sulfimide of the formula

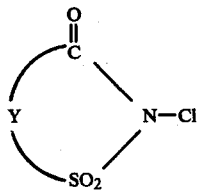

in which Y is o-phenylene, —CH$_2$—CH$_2$—, or —CH$_2$—CH$_2$—CH$_2$—. These compounds include o-sulfobenzoic N-chloroimide, β-sulfopropionic N-chloroimide, and γ-sulfobutyric N-chloroimide.

Also preferred for use as N-chlorohalogenating agents in the preparation of the sulfinyl chlorides in accordance with this invention are N-chloroimides of the formula

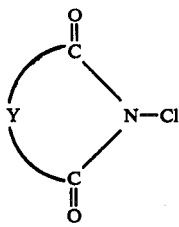

in which Y is o-phenylene, —CH$_2$—CH$_2$—, or —CH$_2$—CH$_2$—CH$_2$—. These compounds include N-chlorophthalimide, N-chlorosuccinimide, and N-chloroglutarimide.

Many of the N-chloro halogenating agents employed in the process of this invention are available commercially, and any of them can be prepared by methods well recognized throughout the chemical arts. Typical of the literature sources which detail preparation of the N-chloro halogenating agents are Bachand et al., *J. Org. Chem.* 39, (1974) pp. 3136–3138; Theilacker et al., *Liebigs Ann. Chem.* 703, (1967) pp. 34–36; and Houben-Weyl, *Methoden der Organischen Chemie*, Volume V/3, pp. 796–810.

N-Chloro halogenating agents which are preferred for use in the process of this invention are N-chloro imides, particularly N-chlorosuccinimide or N-chlorophthalimide, and, especially N-chlorophthalimide.

The N-chloro halogenating agent is generally employed in an amount corresponding to between about 1 mole to about 1.5 moles of the halogenating agent per mole of penicillin α-sulfoxide ester. Larger excesses of the halogenating agent can be employed, however, without advantage. The preferred molar ratio of the N-chloro halogenating agent is between about 1.0 to about 1.1 moles per mole of penicillin α-sulfoxide ester.

Likewise, an excess of the alkylene oxide acid binding agent can be employed and in general the epoxide is used in an amount corresponding to a slight molar excess of the penicillin α-sulfoxide and preferably a 5 to 8 fold excess.

Inert organic solvents which are suitable in the process of this invention include those solvents which are employed in the preparation of the sulfinyl chlorides from the penicillin β-sulfoxide in the known process. Such solvents include the aromatic hydrocarbon solvents, for example, benzene, toluene, xylene, ethyl benzene, cumene, and like aromatic hydrocarbons; halogenated hydrocarbons such as carbon tetrachloride, chlorobenzene, bromoform, bromobenzene, ethylene dichloride, 1,1,2-trichloroethane, ethylene dibromide, and like halogenated hydrocarbons; and the open chain hydrocarbons such as heptane, octane, nonane, decane, and the like. Higher boiling solvents are, however, suitable in the process of this invention but it is convenient to choose one having a boiling point within the range at which the process is carried out as mentioned above. Particularly useful solvents in the process of the invention include benzene, toluene, and 1,1,2-trichloroethane.

In carrying out the process of this invention it is preferable to employ calcium oxide in conjunction with one of the above-described alkylene oxides as disclosed by Ta-Sen Chou in his co-pending application Ser. No. 696,674. Generally, between about 100 g. and about 500 g. of calcium oxide per mole of penicillin α-sulfoxide is used. Preferably between about 200 g. and about 250 g. of calcium oxide per mole of penicillin α-sulfoxide ester are used in the preparation of the 2-chlorosulfinyl azetidin-4-one. The calcium oxide is present throughout the reaction of the penicillin α-sulfoxide with the N-chloro halogenating agent in the presence of the alkylene oxide. Since the calcium oxide is insoluble in the reaction medium it is readily separated after the reaction, for example by filtration.

As mentioned above, the reaction is carried out under anhydrous conditions. Best results are obtained when the penicillin sulfoxide and the solvent employed in the process are dried before use. Any of the conventional methods for drying solvents and compounds can be employed. Solvents can be employed, for example, by azeotropic distillation or by drying over a common drying agent such as anhydrous sodium sulfate or magnesium sulfate. The penicillin α-sulfoxide can be dried in vacuo with heat if desired.

Preferred starting materials employed in the process of this invention, the 6β-acylamido-2,2-dimethylpenam-3-carboxylic acid ester α-sulfoxides, are represented by the following structural formula.

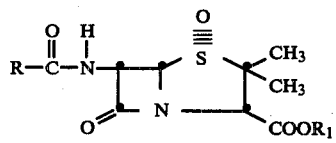

wherein

R is hydrogen, C$_1$–C$_3$ alkyl, halomethyl or cyanomethyl;

or R is the group R' wherein R' is phenyl or phenyl substituted by 1 or 2 substituents selected from the group consisting of C$_1$–C$_4$ alkyl, C$_1$–C$_4$ alkoxy, halo, protected hydroxy, nitro, cyano and trifluoromethyl;

or R is a group of the formula

wherein R" is t-butyl, 2,2,2-trichloroethyl, benzyl, 4-nitrobenzyl or 4-methoxybenzyl;

or R is a group of the formula

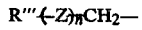

wherein R''' is R' as defined above, 2-thienyl, 3-thienyl, 2-furyl, 3-furyl or 1,4-cyclohexadienyl; n is 0 or 1, and Z is O or S, subject to the limitation that when n is 1, R''' is R';

or R is a substituted aralkyl group of the formula

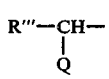

wherein R''' has the same meanings as defined above and Q is protected hydroxy or protected amino; and R$_1$ is a carboxylic acid protecting group.

In the above definition of the penicillin α-sulfoxides, the term "C$_1$–C$_3$ alkyl" refers to methyl, ethyl, n-propyl, and isopropyl; "halomethyl" refers to chloromethyl and bromomethyl.

Illustrative of the substituted phenyl groups represented by the term "R'" in the above formula are 4-methylphenyl, 3-ethylphenyl, 2,4-dimethylphenyl, 4-n-propylphenyl, 4-t-butylphenyl, 2-methoxyphenyl, 4-ethoxyphenyl, 3-isopropoxyphenyl, 4-isobutyloxyphenyl, 4-chlorophenyl, 3,4-dichlorophenyl, 3-chloro-4-fluorophenyl, 4-nitrophenyl, 2-cyanophenyl, 4-trifluoromethylphenyl, and like mono or di-substituted phenyl groups, and the phenyl groups substituted with protected hydroxy are illustrated by such groups as 3-formyloxyphenyl, 4-trityloxyphenyl, 4-benzyloxyphenyl, 3-nitrobenzyloxyphenyl, 4-chloroacetoxyphenyl, and like protected hydroxy-substituted phenyl groups.

Illustrative of the groups represented in the above definition by the term "R—$(Z)_n$—$CH_2$—" are phenoxyphenyl, 4-fluorophenoxymethyl, 3-benzyloxyphenoxymethyl, 4-benzhydryloxyphenoxymethyl, 3-trityloxyphenoxymethyl, 4-nitrobenzyloxyphenoxymethyl, 4-trimethylsilyloxyphenoxymethyl, 3-nitrophenoxymethyl, 4-cyanophenoxymethyl, 4-trifluoromethylphenoxymethyl, 4-n-propylphenoxymethyl, 3-methoxyphenoxymethyl, 4-ethoxyphenoxymethyl, 3,4-dimethylphenoxymethyl, 3,4-dichlorophenoxymethyl, 2-fluorophenoxymethyl, phenylthiomethyl, 4-trimethylsilyloxyphenylthiomethyl, 3-nitrophenylthiomethyl, 4-cyanophenylthiomethyl, 4-trifluoromethylphenylthiomethyl, 2-chlorophenylthiomethyl, 3,4-dichlorophenylthiomethyl, 4-methylphenylthio, 3-methoxyphenylthiomethyl, 2,4-dimethylphenylthiomethyl, 4-benzhydryloxyphenylthiomethyl, 3-trityloxyphenylthiomethyl, 2-thienylmethyl, 3-thienylmethyl, 2-furylmethyl, and 3-furylmethyl.

Illustrative of the groups defined in the above formula wherein R is a substituted arylalkyl group of the formula R'''—CH—(Q)— are α-(benzhydryloxy)-thien-2-ylmethyl, α-(4-nitrobenzyloxy)-thien-2-ylmethyl-, α-(t-butyloxycarbamido)-thien-2-ylmethyl, α-formyloxybenzyl, α-benzyloxybenzyl, α-t-butyloxycarbamidobenzyl, α-(2,2,2-trichloroethoxycarbamido)benzyl, α-(trimethylsilyloxy)-4-bromobenzyl, α-(benzhydryloxycarbamido)-3-chlorobenzyl, α-(benzhydryloxy)-furan-2-ylmethyl, α-(t-butyloxycarbamido)-furan-2-ylmethyl, α-(4-nitrobenzyloxy)-2-cyanobenzyl, α-formyloxy-4-methylbenzyl, α-(benzyloxycarbamido)-4-methoxybenzyl, and α-(trimethylsilylamino)benzyl.

In the above formula, $R_1$ represents a carboxylic acid-protecting group. Such groups are those ester-forming groups commonly employed in the cephalosporin antibiotic art to block or protect the $C_4$ carboxylic acid function of a molecule while a reaction or sequence of reactions involving other sites in the molecule are carried out. These protecting groups are readily removed by cleavage under acidic hydrolysis conditions or under conditions of hydrogenolysis. Examples of such carboxylic acid-protecting ester groups are t-butyl, the haloalkyl ester groups such as the trihaloalkyl groups, for example 2,2,2-trichloroethyl and the monohaloalkyl groups such as 2-iodoethyl; the benzyl type ester protecting groups, for example benzyl, 4-methoxybenzyl, 4-nitrobenzyl, and 3,5-dimethoxybenzyl; the diarylalkyl protecting groups such as diphenylmethyl and 4,4'-dimethoxydiphenylmethyl; and other recognized protecting groups, for example phenacyl, p-halophenacyl such as p-chlorophenacyl, and the succinimidomethyl ester forming group. The $R_1$ protecting groups function in the improved process of this invention merely as carboxylic acid-protecting groups and are not critical to the process. Other commonly recognized carboxylic acid-protecting groups can be employed, for example those described by E. Haslam in *Protective Groups in Organic Chemistry*, J. F. W. McOmie, ed., Plenum Press, N.Y., 1973, chapter 5. Preferred ester groups represented by the term $R_1$ in the process of this invention are t-butyl, diphenylmethyl, p-methoxybenzyl, and p-nitrobenzyl. The p-nitrobenzyl ester is an especially preferred carboxylic acid protecting group of this invention.

The term "protected-hydroxy" in the above formula refers to the commonly employed hydroxy-protecting groups which are readily removable. Such groups include, for example, the formyloxy group, acetoxy, chloroacetoxy, benzyloxy, p-nitrobenzyloxy, trityloxy, and the trimethylsilyloxy group. As with the above-described carboxylic acid protecting groups, the hydroxy-protecting groups function merely as blocking groups to avoid unnecessary side reactions during the process of this invention. Such groups are therefore not critical to the process of this invention and other groups in addition to those mentioned above would be recognized by those skilled in the art, for example those described by C. D. Reese in *Protecting Groups in Organic Chemistry*, supra, chapter 3.

The term "protected amino" employed in the above definition of the preferred starting materials in the present process refers to a substituted amino group wherein the substituent is one of the commonly employed amino blocking or protecting groups used in the cephalosporin and penicillin arts. For example, the amino-protecting group is one which is readily removed following the process of this invention under conditions of acidic or basic hydrolysis or by hydrogenolysis. Examples of such groups include the groups forming urethanes with the amino group, for example the t-butyloxycarbonyl group, the benzyloxycarbonyl group, the substituted benzyloxycarbonyl group such as the p-methoxybenzyloxycarbonyl group, and the p-nitrobenzyloxycarbonyl group, the trihaloalkoxycarbonyl group such as 2,2,2-trichloroethoxycarbonyl group, the enamine-forming protecting groups such as the enamine formed with methyl or ethyl acetoacetate, and like recognized amino-protecting groups. Further examples of commonly employed amino-protecting groups are described by J. W. Barton in *Protecting Groups in Organic Chemistry*, supra, chapter 2.

Especially preferred penicillin α-sulfoxide esters used as starting materials in the process of this invention are the esters of 6-phenoxyacetamido-2,2-dimethylpenam-3-carboxylic acid α-sulfoxide, 6-phenylacetamido-2,2-dimethylpenam-3-carboxylic acid α-sulfoxide, and 6-(2-thienyl)acetamido-2,2-dimethylpenam-3-carboxylic acid α-sulfoxide. Preferred esters of the above compounds are the p-nitrobenzyl ester, the p-methoxybenzyl ester, the diphenylmethylester and the 2,2,2-trichloroethyl esters.

The process of this invention is carried out by mixing calcium oxide and molar equivalents of the penicillin α-sulfoxide and the N-chloro halogenating agent in a suitable pre-dried solvent. The alkylene oxide is then added and the mixture is heated to a temperature between about 70° and about 120° C.

The 2-chlorosulfinylazetidin-4-one compounds provided by the process of this invention are employed in the subsequent process for the preparation of 7-acylamido-3-exomethylenecepham-4-carboxylic acid ester β-sulfoxides as described by Kukolja in co-pending application Ser. No. 673,036. As described therein the 2-chlorosulfinyl ester is reacted in an inert solvent with a Lewis acid Friedel-Crafts type catalyst to effect the intramolecular cyclization with formation of the 7-acylamido-3-exomethylenecepham-4-carboxylic acid ester β-sulfoxide. Accordingly, the products provided by the process of the present invention need not be isolated but are conveniently left in a filtered reaction product mixture and poured into an inert solvent containing the Friedel-Crafts catalyst to effect the cyclization according to Kukolja.

In a preferred embodiment of the process of this invention, p-nitrobenzyl 6-phenoxyacetamido-2,2-dimethylpenam-3-carboxylate α-sulfoxide is mixed in dry benzene with N-chlorophthalimide and calcium oxide is added and the mixture is heated. Propylene oxide is added to the warm mixture and thereafter the mixture is heated at the boiling point for about 2 hours. The reaction mixture is cooled in an ice-bath and preferably after dilution with a hydrocarbon solvent such as pentane or petroleum ether and is then filtered. The cold filtrate containing the 2-chlorosulfinylazetidin-4-one ester is poured into a dry solution of the Friedel-Crafts catalyst, preferably stannic chloride, in an inert hyrocarbon solvent, for example pentane pre-cooled to ice-bath temperature. The reaction mixture is stirred in the cold for about one hour and then is allowed to warm slowly to room temperature with stirring. The reaction mixture is stirred for about 6 to about 12 hours at room temperature and the light yellow precipitate, a complex formed with the stannic chloride, is filtered and dried under vacuum. The dry precipitate is dissolved in methyl alcohol and the solution is stirred for about 3 hours at ice-bath temperature. p-Nitrobenzyl 7-phenoxyacetamido-3-exomethylenecepham-4-carboxylate β-sulfoxide forms as a precipitate from the solution and to insure complete precipitation, the solution is allowed to stand in the cold overnight. The precipitate is filtered and the product is dried under vacuum.

Examples of sulfinyl chlorides prepared by the process of this invention include:

t-butyl 3-methyl-2-(2-chlorosulfinyl-4-oxo-3-phenylacetamido-1-azetidinyl)-3-butenoate;

t-butyl 3-methyl-2-(2-chlorosulfinyl-4-oxophenoxyacetamido-1-azetidinyl)-3-butenoate;

benzyl 3-methyl-2-(2-chlorosulfinyl-4-oxo-3-formamido-1-azetidinyl)-3-butenoate;

2,2,2-trichloroethyl 3-methyl-2-(2-chlorosulfinyl-4-oxo-3-acetamido-1-azetidinyl)-3-butenoate;

p-nitrobenzyl 3-methyl-2-(2-chlorosulfinyl-4-oxo-3-butyramido-1-azetidinyl)-3-butenoate;

p-methoxybenzyl 3-methyl-2-(2-chlorosulfinyl-4-oxo-3-chloroacetamido-1-azetidinyl)-3-butenoate;

benzhydryl 3-methyl-2-[2-chlorosulfinyl-4-oxo-3-cyanoacetamido-1-azetidinyl]-3-butenoate;

p-nitrobenzyl 3-methyl-2-[2-chlorosulfinyl-4-oxo-3-(4-nitrobenzyloxycarbamido)-1-azetidinyl]-3-butenoate;

t-amyl 3-methyl-2-(2-chlorosulfinyl-4-oxo-3-benzyloxycarbamido-1-azetidinyl)-3-butenoate;

2-iodoethyl 3-methyl-2-[2-chlorosulfinyl-4-oxo-3-(2',2',2'-trichloroethoxycarbamido)-1-azetidinyl]-3-butenoate;

benzyl 3-methyl-2-[2-chlorosulfinyl-4-oxo-3-(2'-thienylacetamido)-1-azetidinyl]-3-butenoate;

t-amyl 3-methyl-2-(2-chlorosulfinyl-4-oxo-3-benzamido-1-azetidinyl)-3-butenoate;

phenacyl 3-methyl-2-[2-chlorosulfinyl-4-oxo-3-(4'-chlorobenzamido)-1-azetidinyl]-3-butenoate;

p-chlorophenacyl 3-methyl-2-[2-chlorosulfinyl-4-oxo-3-(3'-formyloxybenzamido)-1-azetidinyl]-3-butenoate;

succinimidomethyl 3-methyl-2-[2-chlorosulfinyl-4-oxo-3-(4'-trifluoromethylbenzamido)-1-azetidinyl]-3-butenoate;

phthalimidomethyl 3-methyl-2-[2-chlorosulfinyl-4-oxo-3-(3'-methylbenzamido)-1-azetidinyl]-3-butenoate;

t-butyl 3-methyl-2-[2-chlorosulfinyl-4-oxo-3-(2'-methoxybenzamido)-1-azetidinyl]-3-butenoate;

p-nitrobenzyl 3-methyl-2-[2-chlorosulfinyl-4-oxo-3-(1',4'-cyclohexadienylacetamido)-1-azetidinyl]-3-butenoate;

2,2,2-trichloroethyl 3-methyl-2-[2-chlorosulfinyl-4-oxo-3-(2'-thienylacetamido)-1-azetidinyl]-3-butenoate;

p-methoxybenzyl 3-methyl-2-(2-chlorosulfinyl-4-oxo-3-phenylacetamido-1-azetidinyl)-3-butenoate;

2,2,2-trichloroethyl 3-methyl-2-(2-chlorosulfinyl-4-oxo-3-phenoxyacetamido-1-azetidinyl)-3-butenoate;

p-nitrobenzyl 3-methyl-2-[2-chlorosulfinyl-4-oxo-3-(2',5'-dichlorophenylacetamido)-1-azetidinyl]-3-butenoate;

benzyl 3-methyl-2-[2-chlorosulfinyl-4-oxo-3-(3'-bromophenoxyacetamido)-1-azetidinyl]-3-butenoate;

p-nitrobenzyl 3-methyl-2-[2-chlorosulfinyl-4-oxo-3-(2'-nitrophenylacetamido)-1-azetidinyl]-3-butenoate;

p-methoxybenzyl 3-methyl-2-[2-chlorosulfinyl-4-oxo-3-(4'-nitrophenoxyacetamido)-1-azetidinyl]-3-butenoate;

benzhydryl 3-methyl-2-[2-chlorosulfinyl-4-oxo-3-(3'-cyanophenylacetamido)-1-azetidinyl]-3-butenoate;

p-bromophenacyl 3-methyl-2-[2-chlorosulfinyl-4-oxo-3-(2'-cyanophenoxyacetamido)-1-azetidinyl]-3-butenoate;

2,2,2-tribromoethyl 3-methyl-2-[2-chlorosulfinyl-4-oxo-3-(3'-trifluoromethylphenoxyacetamido)-1-azetidinyl]-3-butenoate;

t-butyl 3-methyl-2-[2-chlorosulfinyl-4-oxo-3-(3'-ethoxyphenylacetamido)-1-azetidinyl]-3-butenoate;

p-nitrobenzyl 3-methyl-2-[2-chlorosulfinyl-4-oxo-3-(4'-isopropoxyphenoxyacetamido)-1-azetidinyl]-3-butenoate;

p-nitrobenzyl 3-methyl-2-[2-chlorosulfinyl-4-oxo-3-(α-formyloxyphenylacetamido)-1-azetidinyl]-3-butenoate;

p-methoxybenzyl 3-methyl-2-[2-chlorosulfinyl-4-oxo-3-(α-benzhydryloxyphenylacetamido)-1-azetidinyl]-3-butenoate;

benzyl 3-methyl-2-[2-chlorosulfinyl-4-oxo-3-(2-thienyl-α-benzyloxyacetamido)-1-azetidinyl]-3-butenoate;

benzhydryl 3-methyl-2-[2-chlorosulfinyl-4-oxo-3-(α-benzhydryloxyphenylacetamido)-1-azetidinyl]-3-butenoate;

p-nitrobenzyl 3-methyl-2-[2-chlorosulfinyl-4-oxo-3-(α-benzyloxycarbonylaminophenylacetamido)-1-azetidinyl]-3-butenoate;

t-butyl 3-methyl-2-[2-chlorosulfinyl-4-oxo-3-(α-t-butyloxycarbonylaminophenylacetamido)-1-azetidinyl]-3-butenoate;

p-nitrobenzyl 3-methyl-2-[2-chlorosulfinyl-4-oxo-3-(2-thienyl-α-p-nitrobenzyloxycarbonylaminoacetamido)-1-azetidinyl]-3-butenoate;

p-nitrobenzyl 3-methyl-2-[2-chlorosulfinyl-4-oxo-3-(2'-thienylacetamido)-1-azetidinyl]-3-butenoate;

benzyl 3-methyl-2-[2-chlorosulfinyl-4-oxo-3-(3'-thienylacetamido)-1-azetidinyl]-3-butenoate;

p-methoxybenzyl 3-methyl-2-[2-chlorosulfinyl-4-oxo-3-phenylthioacetamido-1-azetidinyl]-3-butenoate;

benzhydryl 3-methyl-2-[2-chlorosulfinyl-4-oxo-3-(2',5'-dichlorophenylthioacetamido)-1-azetidinyl]-3-butenoate;

p-nitrobenzyl 3-methyl-2-[2-chlorosulfinyl-4-oxo-3-(3'-nitrophenylthioacetamido)-1-azetidinyl]-3-butenoate;

p-nitrobenzyl 3-methyl-2-[2-chlorosulfinyl-4-oxo-3-(2'-cyanophenylthioacetamido)-1-azetidinyl]-3-butenoate; and p-methoxybenzyl 3-methyl-2-[2-chlorosulfinyl-4-oxo-3-(4'-trifluoromethylphenylthioacetamido)-1-azetidinyl]-3-butenoate.

The 6-acylamido-2,2-dimethylpenam-3-carboxylic acid ester α-sulfoxides employed in the process of this invention are prepared by the oxidation of the corresponding 6-acylamido-2,2-dimethylpenam-4-carboxylic acid ester with ozone according to the procedure described by Spry, *J. Org. Chem.*, 37, No. 5, 794 (1972). In general, the 6-acylamido-2,2-dimethylpenam-3-carboxylic acid is reacted at a temperature of about $-10°$ C. to about $+5°$ C. in an aqueous organic solvent mixture, for example acetone-water with excess ozone and the course of the sulfoxide formation followed by thin layer chromatography. When this layer chromatography shows no further evidence of starting material, the reaction mixture is purged with air and the water miscible organic solvent is evaporated under reduced pressure leaving an aqueous concentrate. The β-sulfoxide formed in the oxidation is considerably less soluble in the aqueous concentrate than is the α-sulfoxide and forms a precipitate. The β-sulfoxide is separated from the aqueous concentrate containing the α-sulfoxide, for example by filtration or by centrifugation. The aqueous filtrate containing the α-sulfoxide is then extracted with a suitable organic solvent, for example ethyl acetate. The extract is dried and is then evaporated in vacuo to afford the 6-acylamido-2,2-dimethylpenam-3-carboxylic acid α-sulfoxide.

A suitable TLC system which can be used to follow the course of the oxidation is iso-amyl acetate:-iso-propyl acetate-acetic acid, 3:2:1.

The β-sulfoxide isomer is formed in greater abundance than is the α-sulfoxide; however, the isomers are readily separated owing to their different solubilities in aqueous medium.

Prior to this invention, the penicillin sulfoxides employed in the preparation of 2-chlorosulfinylazetidin-4-ones for use in the preparation of 3-exomethylenecepham sulfoxides was carried out with the penicillin β-sulfoxide. It is known that the commonly employed methods for preparing penicillin sulfoxides by the oxidation of a penicillin with a peracid affords the β-sulfoxide. For example, the oxidation of a penicillin with a peracid such as peracetic acid or m-chloroperbenzoic acid affords only the β-sulfoxide thereof.

This invention comprises the discovery that the use of a 6-acylamido-2,2-dimethylpenam-3-carboxylic acid ester α-sulfoxide affords higher yields of 2-chlorosulfinylazetidin-4-one intermediates which on direct conversion in the Kukolja process described above afford higher yields of pure 7-acylamido-3-exomethylenecepham-4-carboxylic acid ester β-sulfoxide.

The following examples further illustrate the process of this invention.

EXAMPLE 1

Preparation of penicillin V α-sulfoxide

A solution of 17.5 g. (0.05 M) of 6-phenoxyacetamidopenicillanic acid in 1 liter of 1:1 acetone:water was cooled to 0° C. and ozone was introduced into the cold solution via an inlet positioned well below the surface of the solution. The solution was stirred vigorously during the addition of ozone and the progress of the reaction was followed by thin layer chromatography. The passage of ozone into the solution was discontinued when the starting material had disappeared on the thin layer. The thin layer chromatograms were carried out on silica gel plates using the system 3:2:1 iso-amyl acetate:iso-propyl acetate:acetic acid. The ozone was generated in a standard ozonator in a stream of air at a rate of 2.7 g. of ozone/120 l. air/hr.

The passage of ozone was continued for six hours before the starting material had disappeared on the thin layer chromatograms. The reaction mixture was then purged with air for approximately 15 minutes and the acetone was removed under vacuum. The β-sulfoxide of 6-phenoxyacetamidopenicillanic acid crystallized from the aqueous concentrate and was separated by filtration. The yield of β-sulfoxide was approximately 50 percent. The filtrate containing the α-sulfoxide was extracted with an equal volume of ethyl acetate. The ethyl acetate extract was separated from the aqueous phase and was dried by shaking the extract with sodium chloride solution. The extract was evaporated to dryness to yield the α-sulfoxide as a foam in approximately 40 percent yield.

EXAMPLE 2

Alternative isolation method for penicillin V α-sulfoxide

The α-sulfoxide prepared as described above was isolated in an alternative method as follows. Following the oxidation of the same amount of penicillin V in the same quantity and proportions of acetone and water and employing the same flow rate of ozone in air, the reaction mixture was evaporated in vacuo as before to obtain an aqueous concentrate. The β-sulfoxide which crystallized was filtered and the aqueous filtrate containing the α-sulfoxide was seeded and then evaporated under reduced pressure to approximately one-half of its original volume. The α-sulfoxide crystallized from the seeded concentrate. The average yield of the α-sulfoxide obtained in a number of runs by this alternative isolation procedure was between about 30 and 34 percent.

Alternatively, the aqueous filtrate containing the α-sulfoxide, obtained as described above, was extracted twice with ethyl acetate. The extracts were combined and were washed with a saturated solution of sodium chloride. The washed extract was concentrated by evaporation to about half the original volume. The α-sulfoxide crystallized from the concentrate. The average yield of the α-sulfoxide obtained in a number of runs was 33 to 35 percent. The crystalline α-sulfoxide melts at about 149° C., $[\alpha]_D^{25°} + 168.8°$ (acetone, C $5 \times 10^{-5}$ g/ml).

EXAMPLE 3

Preparation of p-nitrobenzyl 6-phenoxyacetamidopenicillanate α-sulfoxide

To a solution of 7.5 g. (0.0205 M) of 6-phenoxyacetamidopenicillanic acid α-sulfoxide in 30 ml. of dry acetone were added 2.88 ml. (0.0205 M) of triethylamine and 4.86 g. (10 percent excess) of p-nitrobenzyl bromide. The solution was stirred for 24 hours and thereafter 15 ml. of water were added dropwise and stirring was continued for an additional 15 minutes. The product, p-nitrobenzyl 6-phenoxyacetamidopenicillanate α-sulfoxide, crystallized from the diluted reaction mixture and was filtered. The product was washed on the filter with 20 ml. of 1:1 acetone:water followed by three 20 ml. water washed and finally again with a 20 ml. 1:1 acetone:water wash. The product was dried under vacuum at room temperature. The dried product weighed 7.6 g. (74.1 percent). Melting point 129° C., $[\alpha]_D^{25}+130.9$ (CHCl$_3$, C, $8\times10^{-5}$ g/ml).

EXAMPLE 4 p-Nitrobenzyl 7-phenoxyacetamido-3-exomethylenecepham-4-carboxylate 1-oxide

Two liters of reagent grade benzene were dried by azeotropic distillation for 2 hours during which 200 ml. were discarded. The benzene was allowed to cool and 25 g. of calcium oxide, 50.2 g. of p-nitrobenzyl 6-phenoxyacetamidopenicillanate α-sulfoxide, and 23 g. of N-chlorophthalimide were added. The reaction flask was equipped with a Dean-Stark trap and as the mixture was heated, 38 ml. of propylene oxide were added. The reaction mixture began boiling at a temperature of 78.5° C. The reaction mixture was heated for 2 hours and 15 minutes during which time 400 ml. were distilled over. The reaction mixture was cooled to a temperature of about 40° C. in an ice-water bath and 100 ml. of pentane were added. Cooling was then continued to a temperature of about 10° C. The nuclear magnetic resonance spectrum (NMR) of the intermediate azetidinone sulfinyl chloride was obtained by withdrawing a small sample of the mixture, evaporating the sample, and then reconstituting the residue in deuterated chloroform. The NMR (CDCl$_3$) of the sulfinyl chloride showed the following signals: delta 1.93 (s, 3H), 4.55 (s, 2H), 5.13-5.03 (m, 3H), 5.33 (s, 2H), 5.57 (d, 1H, J=4.5 Hz), 6.30 (q, 1H, J=4.5 Hz), 7.0-6.8 (m, 5H), 7.2 (d, 2H, J=11 Hz) and 8.23 (d, 2H, J=11 Hz). The reaction mixture was then filtered into 25 ml. of pre-cooled pentane containing 25 ml. of reagent grade stannic chloride. A light orange complex formed in the mixture. The mixture was stirred 1 hour at ice bath temperature and overnight at room temperature. The orange complex was filtered and washed with n-pentane and was dried on the filter. The dried granular precipitate was then slowly added to 300 ml. of methyl alcohol. A white precipitate of p-nitrobenzyl 7-phenoxyacetamido-3-exomethylenecepham-4-carboxylate sulfoxide formed immediately. The suspension was stirred at ice bath temperature for 7.5 hours and was then stored in the refrigerator overnight to insure complete precipitation of the product. The product was filtered and dried and weighed 37.66 g. (75.4 percent yield by weight) and melted at 191°-193° C. The percent purity by HPLC was 99.5 percent (corrected yield 75.0 percent).

EXAMPLE 5

Ring-expansion with N-chlorosuccinimide

One liter of reagent grade benzene was distilled for 2½ hours during which 100 ml. of distillate was removed and discarded. The benzene was cooled and 12.5 g. of calcium oxide, 25 g. of p-nitrobenzyl 6-phenoxyacetamidopenicillanate α-sulfoxide, and 7.6 g. of N-chlorosuccinimide were added. The mixture was heated while 18 ml. of propylene oxide was added to the boiling point. After the propylene oxide was added, the boiling point of the reaction mixture was 78.5° C. Heating was continued for 2 hours and 15 minutes during which time 260 ml. of distillate were collected. The reaction mixture was then cooled to about 10° C. and was filtered. The reaction mixture was diluted with 50 ml. of pentane at a temperature of about 30° C. and was then added to 25 ml. of pre-cooled pentane containing 12.5 ml. of reagent grade stannic chloride. A light yellow complex formed in the mixture which was stirred for 1 hour at ice bath temperature and then overnight at room temperature. The complex was filtered and dried in vacuo. The dried filter cake weighed 59.35 g. and purity by HPLC was 96.5 percent. The filter cake was slowly dissolved in 50 ml. of methyl alcohol and the mixture stirred for 3 hours at ice bath temperature. The cold mixture was then stored in the refrigerator overnight. The suspension was then filtered to yield 16.7 g. (66.8 percent yield), purity by HPLC=96.5 percent (corrected yield 64.4 percent).

We claim:

1. In the process for preparing a 2-chlorosulfinylazetidin-4-one of the formula

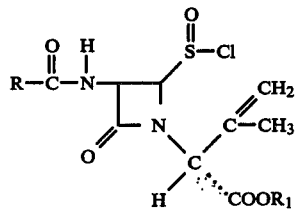

wherein R$_1$ is a conventional carboxylic acid protecting group, which comprises heating under anhydrous conditions in an inert solvent a 6-acylamido-2,2-dimethylpenam-3-carboxylic acid ester β-sulfoxide with an N-chloro halogenating agent in the presence of an alkylene oxide, the improvement which comprises heating at a temperature between about 70° C. and about 120° C. a 6-acylamido-2,2-dimethylpenam-3-carboxylic acid ester α-sulfoxide of the formula

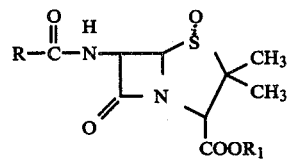

wherein R is phenylmethyl, phenoxymethyl, or 2-thienylmethyl.

2. The process of claim 1 wherein R$_1$ is t-butyl, 2,2,2-trichloroethyl, 2-iodoethyl, benzyl, 4-nitrobenzyl, 4-methoxybenzyl, or diphenylmethyl.

3. The process of claim 2 wherein $R_1$ is 4-nitrobenzyl, 4-methoxybenzyl or diphenylmethyl.

4. The process of claim 1 wherein the alkylene oxide is propylene oxide or butylene oxide.

5. The process of claim 1 wherein the N-chloro halogenating agent is a compound of the formula

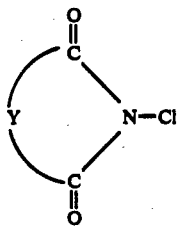

wherein Y is o-phenylene, —CH$_2$—CH$_2$—, or —CH$_2$—CH$_2$—CH$_2$—.

6. The process of claim 5 wherein the N-chloro halogenating agent is N-chlorosuccinimide.

7. The process of claim 5 wherein the N-chloro halogenating agent is N-chlorophthalimide.

8. The process of claim 1 wherein the 6-acylamido-2,2-dimethylpenam-3-carboxylic acid ester α-sulfoxide is heated in the presence of between about 100 grams and about 500 grams of calcium oxide per mole of said α-sulfoxide ester.

9. The process of claim 1 wherein the inert solvent is benzene or toluene.

10. The process of claim 1 wherein p-nitrobenzyl 6-phenoxyacetamido-2,2-dimethylpenam-4-carboxylate α-sulfoxide is heated in benzene at a temperature between about 75° C. and about 80° C. with N-chlorophthalimide in the presence of propylene oxide.

11. The process of claim 1 wherein the α-sulfoxide ester is heated in the presence of between about 100 grams and about 250 grams of calcium oxide per mole of said α-sulfoxide ester.

* * * * *